United States Patent
Chang

(10) Patent No.: US 9,572,851 B2
(45) Date of Patent: Feb. 21, 2017

(54) PHARMACEUTICAL COMPOSITION FOR TREATING DRUG ADDICTION

(75) Inventor: Kaiyi Chang, Yunnan (CN)

(73) Assignee: YUNNAN MINGJINGHENGLI PHARMACEUTICAL CO., LTD. (CN)

( * ) Notice: Subject to any disclaimer, the term of this patent is extended or adjusted under 35 U.S.C. 154(b) by 745 days.

(21) Appl. No.: 13/702,239

(22) PCT Filed: May 26, 2011

(86) PCT No.: PCT/CN2011/000900
§ 371 (c)(1),
(2), (4) Date: Jan. 28, 2013

(87) PCT Pub. No.: WO2011/153819
PCT Pub. Date: Dec. 15, 2011

(65) Prior Publication Data
US 2013/0209593 A1 Aug. 15, 2013

(30) Foreign Application Priority Data
Jun. 7, 2010 (CN) .......................... 2010 1 0192182

(51) Int. Cl.
*A61K 36/28* (2006.01)
*A61K 36/81* (2006.01)
*A61K 36/56* (2006.01)
*A61K 36/185* (2006.01)
*A61K 36/484* (2006.01)

(52) U.S. Cl.
CPC ............. *A61K 36/81* (2013.01); *A61K 36/185* (2013.01); *A61K 36/28* (2013.01); *A61K 36/484* (2013.01); *A61K 36/56* (2013.01)

(58) Field of Classification Search
None
See application file for complete search history.

(56) References Cited

U.S. PATENT DOCUMENTS 3,865,933 A * 2/1975 Mudge ........................ 424/677
2003/0228379 A1 * 12/2003 Shi et al. ..................... 424/725
2005/0100513 A1 5/2005 Watkins

FOREIGN PATENT DOCUMENTS

| CN | 1179949 A | 4/1998 |
|---|---|---|
| CN | 1256925 A | 6/2000 |
| CN | 1416877 A | 5/2003 |
| CN | 101444560 A * | 6/2009 |
| CN | 101698024 A * | 4/2010 |
| WO | WO 0176613 A1 | 10/2001 |

OTHER PUBLICATIONS

Communication pursuant to Article 94(3) EPC dated Nov. 18, 2014 for European Application No. 11791811.0.
Minina, S. A. and Kaukhova, I. E., The Chemistry and Technology of Phytodrugs, Moscow: GEOTAR-Media, 2009, pp. 88 and 124.
Database WPI—Week 200049, Thomson Scientific, London, GB; AN 2000-533654, XP002713908, & CN 1 256 925 A (TU Y), Jun. 21, 2000 (Jun. 21, 2000). Abstract.
Database WPI—Week 200360, Thomson Scientific, London, GB; AN 2003-628051, XP002713909, & CN 1 416 877 A (MO P), May 14, 2003 (May 14, 2003). Abstract.
Database WPI—Week 200175, Thomson Scientific, London, GB; AN 2001-657128, XP002713910, & WO 01/76613 A1 (ZUO Z), Oct. 18, 2001 (20/18/2001). Abstract.
Barthelemy S., "Smoking Cessation: Advice to Smokers", Actualities Pharmaceutiques Oct. 2005 FR, No. 445, Oct. 2005 (Oct. 2005), pp. 27-30 XP009173085, ISSN: 0515-3700, p. 30, middle column.
Djibo A et al; "Intoxication Aigue au Sobi-Lobi (Datura). A Propos de Quatre Cas au Niger = Acute intoxication with sobi-lobi (Datura). Four cases in Niger", Bulletin de la Societe de Patholigie Exotique, FR, vol. 93, No. 4, Nov. 1, 2000 (Nov. 1, 2000), pp. 294-297, XP009173098, ISSN: 0037-9085, entire document.
Khalsa K P S: "Frequently asked questions (FAQ); Low Dose Herbs", Journal of Herbal Pharmacoteraphy, Haworth Herbal Press, Binghamton, US, vol. 7, No. 1, Jan. 1, 2007 (Jan. 1, 2007), pp. 87-98, XP009173084, ISSN: 1522-8940, DOI: 10.1300/J157V07N01_08, entire document.

* cited by examiner

*Primary Examiner* — Terry A McKelvey
*Assistant Examiner* — Catheryne Chen
(74) *Attorney, Agent, or Firm* — Alston & Bird LLP

(57) ABSTRACT

The present invention relates to a pharmaceutical composition for treating drug addiction comprising herb *Gelsemium elegans* Benth. and the flower of herb *Datura metel* L., and optionally any pharmaceutically acceptable excipient, wherein the weight/weight ratio of the raw material of *Gelsemium elegans* Benth. to the raw material of the flower of *Datura metel* is from 2:1 to 6:1.

12 Claims, No Drawings

PHARMACEUTICAL COMPOSITION FOR TREATING DRUG ADDICTION

CROSS-REFERENCE TO RELATED APPLICATIONS

This application is the U.S. National Stage of International Application PCT/CN2011/000900 filed May 26, 2011, which designates the U.S and was published by the International Bureau in Chinese on Dec. 15, 2011, and which claims the benefit of CN 201010192182.9, filed Jun. 7, 2010, both of which are hereby incorporated by reference in their entirety.

TECHNICAL FIELD

The present invention relates to a pharmaceutical composition for treating drug addiction, especially to a pharmaceutical composition comprising Chinese herbs, Herba *Gelsemii Elegantis* (or graceful Jessamine herb, i.e., *Gelsemium elegans* Benth.) and Flos *Daturae Metelis* (or Flos *Daturae*, i.e., the flower of *Datura metel* L.). The present invention further relates to use of Chinese herbs, *Gelsemium elegans* Benth. and the flower of *Datura metel* L., in the manufacture of a medicament for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance.

BACKGROUND ART

In recent years, drugs spread increasingly in the world, and threaten the health of human and peace of international society. The statistic data of World Health Organization (WHO) show that 10 million of people lose normal ability of life and work every year, and more than 100 thousands of people die due to drug abuse every year. WHO divided the substances used as drugs into 8 groups: morphines, barbiturates, alcohols, cocaines, *Cannabis indica*, amphetamines, *Catha edulis* (KHATS) and hallucinogens. Others include nicotine and volatile solutions. The morphines, i.e., opioid, include heroin, morphine, which have potent addiction and resistance, and easily develop dependence after abuse. Heroin widely spreads in the world with huge harm. Traditional detoxification methods include substitution decrement therapy, natural withdrawal therapy, sub-hibernation detoxification therapy, antagonist therapy, and non-drug withdrawal therapies such as electric stimulation, acupuncture, physical treatment, etc. The known drugs for detoxification in the world currently are following kinds: methadone, opioid, buprenorphine, clonidine, britlofex, chlorpromazine, for detoxification treatment of heroin dependence. Most of these drugs belong to opiate receptor agonists and sedative-hypnotic drugs. In practices, opiate receptor agonists such as methadone, buprenorphine are commonly used for substitution decrement treatment, mainly alleviating withdrawal symptoms by replacing drugs to inhibit nervous excitation, being slow in detoxification, easy to change into another dependence, easy in poisoning, and easy in addiction. Non-substitution treatments usually use clonidine, for treatment of light or middle opiate-dependence in drug abusers, having better detoxification effects, and many adverse reactions, being not suitable for long-term use. Hibernation therapy usually uses sedative-hypnotic drugs, but these drugs are of great dose, may injure brain nerves, may imperil life when improper use, and are not good to relieve psychological dependence. Naltrexone used for antagonist therapy is a kind of opiate receptor antagonist, the use of naltrexone after detoxification can greatly reduce euphoria caused by drug abuse, block invigorating effects, prevent relapse, but has no obvious effect in improve protracted symptoms, requires long-term administration, so that many subjects cannot insist.

Long-term of drug abuse may cause physical dependence and psychological dependence in drug abusers. The long-term use of opioid may induce the change of body function state. Nerve cells adapt to the presence of drug and generate tolerance. The drug in vivo has to be kept at a certain level to maintain the stability of physical functions. When drug taking stops or is reduced suddenly, nerve cells may occur derepression, exhibiting a series of withdrawal symptoms such as rhinorrhea, lacrimation, yawn, mydriasis, arrector muscle contraction, perspiration, diarrhea, muscular stiffness, spontaneous ejaculation, elevation of blood pressure, pulsation acceleration, fever, insomnia and anxiety and dysphoria, and accompanying with intensive craving for opioid. The occurrence of withdrawal symptoms indicates the establishment of physical dependence. These withdrawal symptoms make subjects suffer may pains, while chemical drugs usually can well control acute withdrawal symptoms, alleviate or reduce pains. However, after detoxification treatment in subjects with opioid dependence, with the gradual reduction of exogenous opioid, the synthesis of endogenous opioid peptide and the increase of opiate receptor cannot reach normal levels within a short term, physical and psychological discomforts would be sustained for a long term, which are called protracted withdrawal symptoms, mainly manifesting as refractory insomnia, anxiety and dysphoria, ache all over, fatigued and weak, dysthymia. Most of chemical drugs show poor effects in alleviating protracted withdrawal symptoms. Generally, psychological dependence accompanies with physical dependence, and psychological dependence refers to psychological drug craving and inner experience of euphoria reached by repeated drug use in subjects with drug dependence, or called "thinking addiction" or "mind addiction". Being driven by emotion, addicts continuously use drug, thereby change their life style, behavior and personality models. The euphoria and relaxation and tranquility feelings belong to positive reinforcement; while the painful withdrawal symptoms belong to negative reinforcement, inducing reuse of drug to avoid such pains. The two kinds of reinforcement result in addiction in subjects. After acute withdrawal treatment, physical dependence can be eliminated, while psychological dependence can hardly be eliminated, so that relapse rate is relatively high, for example 90% or more as reported, and the reduction of relapse rate is the biggest challenge for detoxification treatment! So far, there is still not a drug for effective treatment of psychological dependence.

Drug abuse is one of public hazards in the world, which is harmful for the abusers and society, and can hardly be withdrawn, has a relatively high relapse rate, and brings tremendous pain and psychological and physical burdens to subjects. Protracted withdrawal symptoms such as malaise and insomnia are main physiological factors for relapse, unappeasable psychological craving for drug is main psychological factor for relapse, drug taking environment and induction from other abusers are main social factors for relapse, so that these psychological, physiological and social factors render easy relapse after detoxification in subjects with heroin dependence. At present, there are near 10 kinds of traditional Chinese drugs for detoxification are approved by State Food and Drug Administration, which are suitable for drug abusers with light, middle drug dependence, wherein the commonly used include "Kangling Tablets" (康灵 片), "Fukang Tablets" (福康片), "Jitai Tablets" (济泰片), "Yianhuishang Oral Solution" (益安回生口服液), "Lingyi Capsules" (灵益胶囊), "Xinsheng Jieduling Soluble Granules" (新生戒毒灵冲剂), "Xiangteng Capsule" (香藤胶囊) and so on. However, these drugs cannot achieve desired effects in treatment of drug abusers with serious drug dependence, and still have to be used in combination with other medicaments.

DESCRIPTION OF THE INVENTION

The present inventors have surprisingly found by conducting experiments that a pharmaceutical composition comprising Chinese herbs, *Gelsemium elegans* Benth. and the flower of *Datura metel* L., in a certain proportion, in a form of their raw materials or an extract thereof can be used for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance, and that the pharmaceutical composition is effective in subjects with various degrees of drug dependence, and can be used alone or in combination with other medicaments. Base on this finding, the inventors have completed the present invention.

In one aspect, the present invention provides use of herb *Gelsemium elegans* Benth. and the flower of herb *Datura metel* L. in the manufacture of a medicament for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance, wherein *Gelsemium elegans* Benth. and the flower of *Datura metel* L. are each used in a form of their raw materials or an extract of the raw material.

In one embodiment of this aspect, the herb *Gelsemium elegans* Benth. and the flower of *Datura metel* L. are each used in a form of their raw materials, wherein the raw material of *Gelsemium elegans* Benth. comprises 70-85% by weight relative to the total weight of the two raw materials, and the raw material of the flower of *Datura metel* L. comprises 30-15% by weight relative to the total weight of the two raw materials; and preferably, the raw material of *Gelsemium elegans* Benth. comprises 70-80% by weight relative to the total weight of the two raw materials and the raw material of the flower of *Datura metel* L. comprises 30-20% by weight relative to the total weight of the two raw materials.

In another embodiment of this aspect, the herb *Gelsemium elegans* Benth. and the flower of *Datura metel* L. are each used in a form of an extract of their raw materials, and the extract can be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

Alternatively, the present invention provides a method for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance, the method comprising administering to the subject with an effective amount of *Gelsemium elegans* Benth. and the flower of *Datura metel* L., wherein *Gelsemium elegans* Benth. and the flower of *Datura metel* L. are each used in a form of their raw materials or an extract of the raw material, and the raw material of *Gelsemium elegans* Benth. comprises 70-85% by weight relative to the total weight of the two raw materials and the raw material of the flower of *Datura metel* L. comprises 30-15% by weight relative to the total weight of the two raw materials; and preferably, the raw material of *Gelsemium elegans* Benth. comprises 70-80% by weight relative to the total weight of the two raw materials and the raw material of the flower of *Datura metel* L. comprises 30-20% by weight relative to the total weight of the two raw materials.

In another aspect, the present invention provides use of *Gelsemium elegans* Benth. and the flower of *Datura metel* L. in the manufacture of a medicament for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance, wherein *Gelsemium elegans* Benth. and the flower of *Datura metel* L. are each used in a form of their raw materials or an extract of the raw material.

In one embodiment of this aspect, the *Gelsemium elegans* Benth. and the flower of *Datura metel* L. are each used in a form of their raw materials, and the weight/weight ratio of *Gelsemium elegans* Benth. to the flower of *Datura metel* L. is from 2:1 to 6:1, preferably from 3:1 to 5:1, and most preferably 4:1.

In another embodiment of this aspect, the *Gelsemium elegans* Benth. and the flower of *Datura metel* L. are each used in a form of an extract of their raw materials, and the extract can be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

Alternatively, the present invention provides a method for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance, the method comprising administering to the subject with an effective amount of *Gelsemium elegans* Benth. and the flower of *Datura metel* L., wherein *Gelsemium elegans* Benth. and the flower of *Datura metel* L. are each used in a form of their raw materials or an extract of the raw material, and the weight/weight ratio of *Gelsemium elegans* Benth. to the flower of *Datura metel* L. is from 2:1 to 6:1, preferably from 3:1 to 5:1, and most preferably 4:1.

In further another aspect, the present invention provides a pharmaceutical composition comprising *Gelsemium elegans* Benth. and the flower of *Datura metel* L., and optionally any pharmaceutically acceptable excipient, wherein *Gelsemium elegans* Benth. and the flower of *Datura metel* L. are each used in a form of their raw materials or an extract of the raw materials, and the raw material of *Gelsemium elegans* Benth. comprises 70-85% by weight relative to the total weight of the two raw materials and the raw material of the flower of *Datura metel* L. comprises 30-15% by weight relative to the total weight of the two raw materials; and preferably, the raw material of *Gelsemium elegans* Benth. comprises 70-80% by weight relative to the total weight of the two raw materials and the raw material of the flower of *Datura metel* L. comprises 30-20% by weight relative to the total weight of the two raw materials.

In one embodiment of this aspect, the *Gelsemium elegans* Benth. and the flower of *Datura metel* L. are each used in a form of their raw materials, and *Gelsemium elegans* Benth. comprises 70-85% by weight relative to the total weight of the two raw materials and the flower of *Datura metel* L. comprises 30-15% by weight relative to the total weight of the two raw materials; and preferably, *Gelsemium elegans* Benth. comprises 70-80% by weight relative to the total weight of the two raw materials and the flower of *Datura metel* L. comprises 30-20% by weight relative to the total weight of the two raw materials.

In one embodiment of this aspect, the *Gelsemium elegans* Benth. and the flower of *Datura metel* L. are each used in a form of an extract of the raw materials, and *Gelsemium elegans* Benth. comprises 70-85% by weight relative to the total weight of the two raw materials and the flower of *Datura metel* L. comprises 30-15% by weight relative to the total weight of the two raw materials; and preferably, *Gelsemium elegans* Benth. comprises 70-80% by weight relative to the total weight of the two raw materials and the flower of *Datura metel* L. comprises 30-20% by weight relative to the total weight of the two raw materials, wherein the extract can be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

In further another aspect, the present invention provides a pharmaceutical composition comprising herb *Gelsemium elegans* Benth. and the flower of herb *Datura metel* L., and optionally any pharmaceutically acceptable excipient, wherein *Gelsemium elegans* Benth. and the flower of *Datura metel* L. are each used in a form of their raw materials or an extract of the raw materials, and the weight/weight ratio of the raw material of *Gelsemium elegans* Benth. to the raw material of the flower of *Datura metel* L. is from 2:1 to 6:1, preferably from 3:1 to 5:1, and most preferably 4:1.

In one embodiment of this aspect, the *Gelsemium elegans* Benth. and the flower of *Datura metel* L. are each used in a form of their raw materials, and the weight/weight ratio of the raw material of *Gelsemium elegans* Benth. to the raw material of the flower of *Datura metel* L. is from 2:1 to 6:1, preferably from 3:1 to 5:1, and most preferably 4:1.

In another embodiment of this aspect, the *Gelsemium elegans* Benth. and the flower of *Datura metel* L. are each used in a form of an extract of their raw materials, and the weight/weight ratio of *Gelsemium elegans* Benth. to the flower of *Datura metel* L. is from 2:1 to 6:1, preferably from 3:1 to 5:1, and most preferably 4:1, wherein the extract can be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

In any of the embodiments of the composition aspect, the composition may further comprise an appropriate amount of other Chinese herbs/medicines, and the other Chinese herbs can be selected from the group consisting of *Glycyrrhiza uralensis* root, *Aucklandia lappa* root and *Areca catechu* fruit, or an extract thereof.

In any of the embodiments of the composition aspect, the composition is useful for eliminating or alleviating acute withdrawal symptoms and protracted symptoms caused by an addictive substance in a subject in need thereof, for eliminating or reducing the degree of desire to obtain the addictive substance in the subject, and for preventing the subject from reusing the addictive substance.

In further aspect, the present invention provides a pharmaceutical composition consisting of herb *Gelsemium elegans* Benth. and the flower of herb *Datura metel* L., and optionally any pharmaceutically acceptable excipient, wherein the *Gelsemium elegans* Benth. and the flower of

*Datura metel* L. are each used in a form of their raw materials or an extract of the raw materials, and the raw material of *Gelsemium elegans* Benth. comprises 70-85% by weight relative to the total weight of the two raw materials and the raw material of the flower of *Datura metel* L. comprises 30-15% by weight relative to the total weight of the two raw materials; and preferably, the raw material of *Gelsemium elegans* Benth. comprises 70-80% by weight relative to the total weight of the two raw materials and the raw material of the flower of *Datura metel* L. comprises 30-20% by weight relative to the total weight of the two raw materials.

In one embodiment of this aspect, the *Gelsemium elegans* Benth. and the flower of *Datura metel* L. are each used in a form of their raw materials, and the raw material of *Gelsemium elegans* Benth. comprises 70-85% by weight relative to the total weight of the two raw materials and the flower of *Datura metel* L. comprises 30-15% by weight relative to the total weight of the two raw materials; and preferably, *Gelsemium elegans* Benth. comprises 70-80% by weight relative to the total weight of the two raw materials and the flower of *Datura metel* L. comprises 30-20% by weight relative to the total weight of the two raw materials.

In another embodiment of this aspect, the *Gelsemium elegans* Benth. and the flower of *Datura metel* L. are each used in a form of an extract of the raw materials, and the raw material of *Gelsemium elegans* Benth. comprises 70-85% by weight relative to the total weight of the two raw materials and the raw material of the flower of *Datura metel* L. comprises 30-15% by weight relative to the total weight of the two raw materials; and preferably, the raw material of *Gelsemium elegans* Benth. comprises 70-80% by weight relative to the total weight of the two raw materials and the raw material of the flower of *Datura metel* L. comprises 30-20% by weight relative to the total weight of the two raw materials, wherein the extract may be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

In further another aspect, the present invention provides a pharmaceutical composition consisting of herb *Gelsemium elegans* Benth. and the flower of herb *Datura metel* L., and optionally any pharmaceutically acceptable excipient, wherein *Gelsemium elegans* Benth. and the flower of *Datura metel* L. are each used in a form of their raw materials or an extract of the raw materials, and the weight/weight ratio of the raw material of *Gelsemium elegans* Benth. to the raw material of the flower of *Datura metel* L. is from 2:1 to 6:1, preferably from 3:1 to 5:1, and most preferably 4:1.

In one embodiment of this aspect, the *Gelsemium elegans* Benth. and the flower of *Datura metel* L. are each used in a form of their raw materials, and the weight/weight ratio of the raw material of *Gelsemium elegans* Benth. to the raw material of the flower of *Datura metel* L. is from 2:1 to 6:1, preferably from 3:1 to 5:1, and most preferably 4:1.

In another embodiment of this aspect, the *Gelsemium elegans* Benth. and the flower of *Datura metel* L. are each used in a form of an extract of their raw materials, and the weight/weight ratio of the raw material of *Gelsemium elegans* Benth. to the raw material of the flower of *Datura metel* L. is from 2:1 to 6:1, preferably from 3:1 to 5:1, and most preferably 4:1, wherein the extract may be a solvent (e.g., water or ethanol) extract of *Gelsemium elegans* Benth. and the flower of *Datura metel* L. alone, or a solvent (e.g., water or ethanol) extract of a mixture of *Gelsemium elegans* Benth. and the flower of *Datura metel* L. In a specific embodiment, the extract of *Gelsemium elegans* Benth. is prepared by the following process: extracting coarse powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting coarse powders of the flower of *Datura metel* L. with water for one or more times, combining the extracts, filtering, concentrating the filtrate to form a thick paste; or extracting coarse powders of the flower of *Datura metel* L. with ethanol for one or more times, combining the extracts, filtering, and concentrating the filtrate to form a thick paste for use.

The term used herein "Herba *Gelsemii Elegantis*", also called as *Gelsemium elegans*, refers to the plant of *Loganiaceae*, *Gelsemium elegans* Benth., and the whole plant may be used, i.e., its root, stem and leaves and whole herb may be used in the invention.

The term used herein "Flos *Daturae Metelis*", also called as *Flos Daturae*, refers to the flower of the plant of *Solanaceae*, *Datura metel* L.

The term used herein "addictive substance" comprises any substances known in the art that may induce physical dependence and psychological dependence, include but are not limited to morphines, barbitals, cocaines, *Cannabis indica*, amphetamines, *catha* (KHAT) and hallucinogens.

The term used herein "effective amount" refers to an amount of the concerned composition when it is administered to a subject in need, it is effective in eliminating or alleviating acute withdrawal symptoms and protracted symptoms caused by an addictive substance in the subject, eliminating or reducing the degree of desire to obtain the addictive substance in the subject, and for preventing the subject from reusing the addictive substance. Those skilled in the art can readily determine and regulate the effective amount according to the disclosures of the present invention.

Those skilled in the art can use the conventional technologies and methods in the art to grind the components of the proportion into powders respectively, and mix them homogenously, or pre-mix the components in advance then grind the mixture in powder, so as to obtain the pharmaceutical composition of the present invention.

Alternatively, those skilled in the art can use the conventional technologies and methods in the art to extract or decoct the components alone or together with a suitable solvent, then combine extracting solutions or decocting solutions to prepare the pharmaceutical composition of the present invention.

The extracts in the pharmaceutical composition of the present invention may be water extracts, alcohol (e.g., methanol, ethanol, propanol, butanol, etc.) extracts or other fat soluble extracts, the extraction method may be any one or a combination of known extraction methods known in the art, including but not being limited to cold soaking extraction, heating and refluxing extraction, ultrasonic extraction, microwave extraction and supercritical extraction.

The simplest and easiest method of using the pharmaceutical composition of the present invention comprises grinding two raw materials, Gelsemium elegans Benth. and the flower of Datura metel L., into fine powders, mixing in a certain proportion, filling to capsules. The two raw materials or extracts thereof may be added with a suitable amount of pharmaceutically acceptable excipients, prepared to from a pharmaceutically acceptable preparation, such as capsules, tablets, granules, pills, powders, troches, teas, etc. According to the desired specific preparation, the pharmaceutical excipient may be selected from suitable diluting agents, absorbing agents, filling agents, dispersing or suspending agents, surfactants, isotonizing agents, thickening agent, emulsifying agents, preservatives, moistening agents, binding agents, disintegrating agents, glidants, lubricants, etc.

The pharmaceutical composition of the present invention may be used for oral administration, and the whole course of treatment is about 20 days. The first phase is withdrawal phase: the withdrawal symptoms of subjects stop from 0.5 h after first administration, the subjects are quiet and lethargy, then may enter bothered phase in which the subjects feel tasteless in smoking and eating, upset, weak, dry mouth, dim eyesight, insomnia, and the subjects at this time usually are in exciting state, tantrum, logorrhea, incoherent, delirium, and may have illusion and consciousness disorders, but have not serious and acute withdrawal symptoms, the subjects would not feel unbearable pains. Where after, the subjects enter a relatively quiet phase, the signs and symptoms of the bothered phase are alleviated or disappear in some extent, especially the subjects are aware of the reduction of illusion and gradually became quiet, refreshed in vitality, appetite and sleep. This phase usually needs about 3 days. The second phase is rehabilitation phase: in this phase, relatively slight protracted symptoms such as dry mouth, dim eyesight, disability, perspiration, palpitation, may occur, and the subjects feel affinity to drugs and drug-abusing mates, then these symptoms would disappear. This phase usually needs about 7 days. The third phase is consolidation phase: the subjects are comprehensively improved in this phase in terms of protracted symptoms such as anxiety, insomnia, poor appetite, palpitation, dysphoria, and have good appetite, sleep, become vigorous, the craving for drugs is substantially eliminated, and normal living habits are restored. This phase usually need about 10 days.

The Gelsemium elegans Benth. and the flower of Datura metel L. used in the present invention are derived from natural plants, contain no addictive contents such as opioid, and are thus not addictive. The pharmaceutical composition of the present invention not only maintains the therapeutic effects for controlling drug abuse, but also has a reduced toxicity by the mutual action, i.e., less toxic and side effects, while maintaining significant therapeutical effects. The pharmaceutical composition of the present invention may effectively alleviate various symptoms during the withdrawal phase, and may effectively eliminate psychological addiction, greatly reduce relapse rate, needs no adjuvant agents, need only a small dose, has a short treatment period, has no addiction, and thus may be used as an excellent medicament for treating drug addiction.

EXEMPLARY MODES FOR CARRYING OUT THE INVENTION

The following examples are only provided to illustrate the present invention, and the scope of the present invention is not limited to these examples.

Example 1

Preparation of Powders 150 g of the raw material of Herba *Gelsemii Elegantis*, 50 g of the raw material of Flos *Daturae* were separately ground to form fine powders, screened, mixed, and sub-packaged in 500 bags, to obtain the target product.

Example 2

Preparation of Capsules (1)

160 g of the raw material of Herba *Gelsemii Elegantis*, 40 g of the raw material of Flos *Daturae* were separately ground to form fine powders, screened, mixed, and packaged in 1000 capsules, to obtain the target product.

Example 3

Preparation of Capsules (2)

160 g of the raw material of Herba *Gelsemii Elegantis*, 40 g of the raw material of Flos *Daturae*, 20 g of *Glycyrrhiza uralensis* were separately ground to form fine powders, screened, mixed, and packaged in 1000 capsules, to obtain the target product.

Example 4

Preparation of Capsules (3)

160 g of the raw material of Herba *Gelsemii Elegantis*, 40 g of the raw material of Flos *Daturae*, 60 g of the raw material of *Glycyrrhiza uralensis* root, 70 g of the raw material of *Aucklandia lappa* root, 70 g of the raw material of *Areca catechu* fruit were provided, in which 30 g of Herba *Gelsemii Etegantis* was ground to form a fine powders for use, the other raw materials and 130 g of Herba *Gelsemii Elegantis* raw material were separately ground to form coarse powders. Flos *Daturae* coarse powders were extracted with ethanol for 3 times, 2 h for each time, all extracting solutions were combined, filtered, the filtrate was concentrated to form a thick paste; the coarse powders of the other raw materials and 130 g of Herba *Gelsemii Elegantis* raw material were combined, extracted with ethanol for 3 times, 2 h for each time, the extracting solutions were combined, filtered, the filtrate was concentrated to form a thick paste; the two above pastes were combined, added with the above fine powder, mixed homogeneously, added with 40 g of dextrin, 60 g of starch, mixed homogenously, granulated, dried, screened, added with 2 g of magnesium stearate, filled in 1000 capsules, to obtain the target product.

Example 5

Preparation of Pills 165 g of the raw material of Herba *Gelsemii Elegantis*, 35 g of the raw material of Flos *Daturae* were separately ground to form fine powders, screened, mixed, and each 100 g of the powders was added with 130 g of refined honey to form small honey pills, to obtain the target product.

Example 6

Preparation of Tablets 155 g of the raw material of Herba *Gelsemii Elegantis*, 45 g of the raw material of Flos *Daturae* were separately ground to form fine powders, screened, mixed, added with 400 g of sucrose powders, 100 g of dextrin, 100 g of starch, mixed homogenously, granulated, dried, screened, added with 10 g of magnesium stearate, pressed to form 2000 tablets, so as to obtain the target product.

Example 7

Preparation of Granules 170 g of the raw material of Herba *Gelsemii Elegantis*, 30 g of the raw material of Flos *Daturae*, wherein Flos *Daturae* and 30 g of Herba *Gelsemii Elegantis* were separately ground to form fine powders for use, the residual 140 g of Herba *Gelsemii Elegantis* was ground to form coarse powders, cold soaked in ethanol overnight, filtered, the filter residue was extracted with ethanol twice under heating and refluxing condition, 2 h for each time, the extracting solutions were combined, filtered, the filtrate was concentrated to form a thick paste; the filter residue was extracted with water for 3 times, 2 h for each time, the extracting solutions were combined, filtered, the filtrate was concentrated to form a thick paste; the two above pastes were combined, added with the above fine powders, mixed homogeneously, added with 40 g of sucrose, 100 g of dextrin, mixed homogenously, granulated, dried, and sub-packaged in 500 bags, to obtain the target product.

Example 8

Preparation of Troches 140 g of the raw material of Herba *Gelsemii Elegantis*, 60 g of the raw material of Flos *Daturae*, wherein Herba *Gelsemii Elegantis* and 30 g of Flos *Daturae* were separately ground to form fine powders for use, the residual 30 g of Flos *Daturae* was ground to form coarse powders, extracted with water under ultrasonic waves for 3 times, 2 h for each time, the extracting solutions were combined, filtered, the, the filtrate was concentrated to form a thick paste, the thick paste was added with the above fine powders, mixed homogeneously, added with 320 g of glutinous rice powder, added with water to form lumps, steamed, mixed with the above powders, pressed to from torches, and dried at a low temperature, to obtain the target product.

Example 9

Preparation of Medicinal Tea 160 g of the raw material of Herba *Gelsemii Elegantis*, 40 g of the raw material of Flos *Daturae*, were separated ground to form coarse powders, the Herba *Gelsemii Elegantis* coarse powders were extracted with ethanol for 3 times, 2 h for each time, the extracting solutions were combined, filtered, the, the filtrate was concentrated to form a thick paste, the filter residue was extracted with water for 3 times, 2 h for each time, the extracting solutions were combined, filtered, the filtrate was concentrated to form a thick paste; the Flos *Daturae* coarse powders were extracted with water under microwaves for 3 times, 2 h for each time, the extracting solutions were combined, filtered, the filtrate was concentrated to form a thick paste; the above 3 thick pastes were combined, added with 200 g of sucrose, 100 g of dextrin relative to per 100 g of raw materials, mixed homogenously to prepare granules, dried, mixed uniformly, and pressed to from blocks, to obtain the target product.

Example 10

Assay of Acute Toxicity

The powders of the raw materials obtained in Example 1 were ground and formulated with distilled water to form a paste with a maximum concentration of 0.3 g/ml, then diluted with distilled water in order to form 4 dose groups with a decreased geometric proportion of 0.75. 60 ICR mice, 18-20 g, (from the Animal Laboratory of Kunming Pharmaceutical Group Incorporated Company), half male and half female, were randomly divided into 6 groups according to gender and bodyweight, 10 mice per group. After fasting without water deprivation for 6 h, except that the blank control group was administered with distilled water, the animals of other groups were separately intragastrically administered once according to the designated doses, and the administration volume was about 40 ml/kg. The immediate responses of mice were observed after administration, died animals were observed by dissection, the survival animals were continuously observed for one week, and the cases of death within one week were recorded. After one week, the animals were dissected and observed, substantive pathological changes were observed, and organs with substantive pathological changes were pathologically examined. Using death number of animals of each group, $LD_{50}$ was calculated by Sun improved Karber's method. The acute toxicity $LD_{50}$ of ICR mice with single intragastric administration was 7.57±1.08 g/kg, 95% confidence interval was 6.57-8.73 g/kg. The maximum tolerable dose was 3.8 g/kg, approximately equivalent to 158 times of the daily dose for a human subject applied clinically.

Example 11

Observation of Clinical Therapeutic Effects 20 subjects with heroin-dependence were treated in clinic, including 18 males and 2 females; and all subjects met the following conditions:

(1) in accordance with diagnostic criteria of CCMD-2-R dependence syndrome as established by Psychiatric Association of Chinese Medical Association;

(2) age: 21-43, average age: 31.4;

(3) heroin abusing history: 2-20 years, average 11.2 years, most with drug-abusing history of 5-20 years;

(4) normal in examinations of blood, urine routine, liver and kidney functions as well as electrocardiogram.

Therapeutic Method:

The treatment was performed in which 2 capsules of the present invention (as prepared according to Example 2) were administered once, twice per day, via 3 days of withdrawal phase, 3 days of rehabilitation phase and 10 days of consolidation phase against relapse. The administration stopped after the end of the course of treatment, and no adjuvant withdrawal drug was used during the course of treatment.

Method for Evaluating Results:

The scoring was performed according to the "Rating Scale of Heroin Protracted Withdrawal Symptoms" as revised by Chinese Drug Dependence Institute of Beijing University, and symptoms in terms of muscle or joint pain, whole body pain, discomfort of four limbs, whole body weakness, poor appetite, palpitation, dysphoria, difficulty of falling asleep, early sleeping, early awakening, were observed, and rated using four scores from 0 to 3, wherein the criteria of severity scores were: 0 for no symptom; 1 for light, inquired, slightly symptom; 2 for middle, presented symptoms, tolerable; 3 for severe, intolerable symptoms.

Clinic Observation Results:

The clinic observation showed that after the course of treatment, all cases exhibited negativity in naloxone induced addiction test, the effective rate of the medicament of the present invention for subjects with heroin dependence was 100%. On the second day after detoxification treatment, the withdrawal symptoms were relatively obvious, the score reached peak value, 8.23±2.15; on the third day, the score of withdrawal symptoms decreased significantly, especially the decrease in terms of symptoms such as weak, anxiety and insomnia was significant, and the score was low and stable after 10 days. The final score of protracted withdrawal symptoms after treatment was 1.95±0.83, close to the level of normal people. During the whole procedure, the scores of symptoms were smaller than those of most of other withdrawal medicaments, and no obvious toxic or side reactions were observed in the treatment. After the end of course of treatment, the subjects did not ask the medicament of the present invention again. During the half year of follow up, except that one subject relapsed after half year, all of other subjects did not relapse, and the relapse rate was merely 5%.

Example 12

Exemplary Cases

Case 1:

Patient Zhang X, male, aged 28, Han nationality, has already taken heroin for 10 years by intravenous injection at an average daily dose of 1 g under the induction of friends, and taken simultaneously diazepam. He was treated according to the method of the present invention using the medicament prepared in Example 2, he became quiet and lethargy on the first day, then was of dysphoria, dry mouth, dim eyesight, divagation, insomnia, on the second day he became logomania, easy to lose temper, showed illusion, on the third day, the withdrawal symptoms such as dim eyesight, dry mouth, divagation, gradually disappeared, illusion disappeared, appetite was improved, psychological state became better, insomnia was alleviated. During the $3^{rd}$ to $10^{th}$ days, "mind addiction" occasionally appeared, after the $10^{th}$ day, he became normal completely. After the end of treatment, he gained 8 kg of bodyweight, and did not relapse in 6 years of follow up.

Case 2:

Patient Song XX, female, aged 36, Han nationality, has already taken heroin for 20 years at a current average daily dose of 0.8 g under the influence of her brother. She was treated according to the method of the present invention using the medicament prepared in Example 2, she became quiet and lethargy on the first day, then she was of dysphoria, perspiration, dry mouth, divagation, insomnia, on the second day she became logomania, easy to lose temper, showed illusion, on the third day, withdrawal symptoms such as perspiration, dry mouth, divagation, gradually disappeared, illusion disappeared, appetite was improved, psychological state became better, insomnia was alleviated. During the $3^{rd}$ to $10^{th}$ days, "mind addiction" occasionally appeared, after the $10^{th}$ day, she became normal completely. After the end of treatment, she gained 6 kg of bodyweight, and did not relapse in 1 year of follow up.

Case 3:

Patient Ma X, male, aged 23, Hui nationality, has already taken heroin for 5 years at a current average daily dose of 1.0 g under the influence of his friends. He was treated according to the method of the present invention using the medicament prepared in Example 4, he became quiet and lethargy on the first day, then he was of dysphoria, insomnia, showed illusion, on the second day he became logomania, divagation, on the third day, withdrawal symptoms such as dysphoria, insomnia, divagation, gradually disappeared, illusion disappeared, appetite was improved, psychological state became better, insomnia was alleviated. During the $3^{rd}$ to $10^{th}$ days, "mind addiction" occasionally appeared, after the $10^{th}$ day, he became normal completely. After the end of treatment, he gained 3 kg of bodyweight, and did not relapse in 8 year of follow up.

Case 4:

Patient Huang X, male, aged 40, Han nationality, has already taken amphetamine chloride for 4 years at an average daily dose of 0.8 g to seek stimulation. He was treated according to the method of the present invention using the medicament prepared in Example 2. He felt upset in the first 3 days, and the feeling of upset gradually disappeared in the following 3-10 days, then the treatment was terminated. After the end of treatment, he gained 3 kg of bodyweight, and did not relapse in 1 year of follow up.

Case 5:

Patient Xiao XX, male, aged 26, Han nationality, has already taken cocaine for half a year with taking cocaine for many times per day from the beginning due to mental vacancy and induction of other people. He was treated according to the method of the present invention using the medicament prepared in Example 2. He felt upset in the first 10 days, perspiration sometimes, and the feeling of upset gradually disappeared after 10 days. The treatment was terminated after 20 days. After the end of treatment, he had a good mental status, and did not relapse in half year of follow up.

Case 6:

Patient Li XX, male, aged 19, Han nationality, has already taken dancing outreach for 4 years with several tablets of dancing outreach per day from the beginning due to the induction of friends in a ballroom. He was treated according to the method of the present invention using the medicament prepared in Example 2. He felt upset in the first 10 days, and the feeling of upset gradually disappeared after 10 days. The treatment was terminated after 20 days. After the end of treatment, he had a good mental status, and did not relapse in 10 months of follow up.

What is claimed is:

1. A method for eliminating or alleviating acute withdrawal symptoms and protracted syndromes caused by an addictive substance in a subject in need thereof, for eliminating or reducing the degree of desire to obtain the addictive substance in the subject, and preventing the subject from reusing the addictive substance, said method comprising administering to said subject an effective amount of a plant *Gelsemium elegans* Benth. and a flower of plant *Datura metel* L., the weight/weight ratio is from 4:1 to 6:1 wherein the plant *Gelsemium elegans* Benth. and the flower of *Datura metel* L. are each used in a form of its raw material or a form of an extract of the raw material.

2. The method of claim 1, wherein the *Gelsemium elegans* Benth. and the flower of *Datura metel* L. are each used in the form of an extract of their raw materials, and the extract of *Gelsemium elegans* Benth. is prepared by the following process: extracting crude powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting crude powders of the flower of *Datura metel* L. with water for one or more times, combining the extracts, filtering, concentrating the filtrate to form a thick paste; or extracting crude powders of the flower of *Datura metel* L. with ethanol for one or more times, combining the extracts, filtering, and concentrating the filtrate to form a thick paste for use.

3. The method of claim 1, wherein the addictive substance is selected from the group consisting of morphines, barbitals, cocaines, *Cannabis indica*, amphetamines, KHATs and hallucinogens.

4. A pharmaceutical composition comprising plant *Gelsemium elegans* Benth. and the flower of plant *Datura metel* L., and optionally any pharmaceutically acceptable excipient, wherein the plant *Gelsemium elegans* Benth. and the flower of plant *Datura metel* L. are each used in a form of its raw material or a form of an extract of the raw material, and the weight/weight ratio of the raw material of *Gelsemium elegans* Benth. to the raw material of the flower of *Datura metel* L. is from 4:1 to 6:1, and said pharmaceutical composition is useful for eliminating or alleviating acute withdrawal symptoms and protracted syndromes caused by an addictive substance in a subject in need thereof and for eliminating or reducing the degree of desire to obtain the addictive substance in the subject.

5. The pharmaceutical composition of claim 4, wherein the weight/weight ratio of the raw material of *Gelsemium elegans* Benth. to the raw material of the flower of *Datura metel* L. is 4:1.

6. The pharmaceutical composition of claim 4, wherein the *Gelsemium elegans* Benth. and the flower of *Datura metel* L. are each used in the form of an extract of their raw materials, and the extract of *Gelsemium elegans* Benth. is prepared by the following process: extracting crude powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting crude powders of the flower of *Datura metel* L. with water for one or more times, combining the extracts, filtering, concentrating the filtrate to form a thick paste; or extracting crude powders of the flower of *Datura metel* L. with ethanol for one or more times, combining the extracts, filtering, and concentrating the filtrate to form a thick paste for use.

7. The pharmaceutical composition of claim 4, wherein the addictive substance is selected from the group consisting of morphines, barbitals, cocaines, *Cannabis indica*, amphetamines, KHATs and hallucinogens.

8. The pharmaceutical composition of claim 4, wherein the pharmaceutical composition further comprises one or more of *Glycyrrhiza uralensis* root, *Aucklandia lappa* root and *Areca catechu* fruit.

9. A pharmaceutical composition consisting of plant *Gelsemium elegans* Benth. and the flower of plant *Datura metel* L., and optionally any pharmaceutically acceptable excipient, wherein the plant *Gelsemium elegans* Benth. and the flower of plant *Datura metel* L. are each used in a form of its raw material or a form of an extract of the raw material, and the weight/weight ratio of the raw material of *Gelsemium elegans* Benth. to the raw material of the flower of *Datura metel* L. is from 4:1 to 6:1, and said pharmaceutical composition is useful for eliminating or alleviating acute withdrawal symptoms and protracted syndromes caused by an addictive substance in a subject in need thereof and for eliminating or reducing the degree of desire to obtain the addictive substance in the subject.

10. The pharmaceutical composition of claim 9, wherein the weight/weight ratio of the raw material of *Gelsemium elegans* Benth. to the raw material of the flower of *Datura metel* L. is 4:1.

11. The pharmaceutical composition of claim 9, wherein the *Gelsemium elegans* Benth. and the flower of *Datura metel* L. are each used in the form of an extract of their raw materials, and the extract of *Gelsemium elegans* Benth. is prepared by the following process: extracting crude powders of *Gelsemium elegans* Benth. with ethanol for one or more times, combining the extracts, filtering, concentrating the filtrate to form a thick paste; extracting the residue with water for one or more times, combining the extracts, filtering, concentrating the filtrate to form a thick paste; and then combining the thick pastes for use; and the extract of the flower of *Datura metel* L. is prepared by the following process: extracting crude powders of the flower of *Datura metel* L. with water for one or more times, combining the extracts, filtering, concentrating the filtrate to form a thick paste; or extracting crude powders of the flower of *Datura metel* L. with ethanol for one or more times, combining the extracts, filtering, and concentrating the filtrate to form a thick paste for use.

12. The pharmaceutical composition of claim 9, wherein the addictive substance is selected from the group consisting of morphines, barbitals, cocaines, *Cannabis indica*, amphetamines, KHATs and hallucinogens.

* * * * *